United States Patent [19]
Yang et al.

[11] Patent Number: 5,571,708
[45] Date of Patent: Nov. 5, 1996

[54] THROMBIN-ACTIVATABLE PLASMINOGEN ACTIVATOR

[75] Inventors: Wen-Pin Yang, Lawrenceville; Gary R. Matsueda, Princeton; Shyh-Yu Shaw, Plainsboro, all of N.J.

[73] Assignee: Bristol-Myers Squibb Company, Princeton, N.J.

[21] Appl. No.: 49,195

[22] Filed: Apr. 19, 1993

[51] Int. Cl.$^6$ .......................... C12P 21/08; A61K 38/48; C07K 16/00; C07H 19/00

[52] U.S. Cl. .................. 435/215; 424/94.63; 424/192.1; 435/7.1; 435/188.5; 435/212; 435/214; 435/217; 530/387.3; 536/22.1; 536/23.1; 536/23.2; 536/23.4; 536/23.53

[58] Field of Search .............................. 424/94.63, 192.1; 435/188.5, 214, 215, 217, 69.7, 7.1, 212; 530/387.3; 536/22.1, 23.1, 23.2, 23.4, 23.53

Primary Examiner—Robert A. Wax
Assistant Examiner—Hyosuk Kim
Attorney, Agent, or Firm—Thomas R. Savitsky; Timothy J. Gaul

[57] ABSTRACT

A new chimeric plasminogen activator with high fibrin affinity was designed to bind to a fibrin clot and initiate clot destruction in the presence of thrombin, but not plasmin. The chimeric molecule has an antibody variable region having a fibrin-specific antigen binding site and a single chain urokinase region having a thrombin activation site but not a plasmin activation site. The preferred embodiment, 59D8-ScuPA-T, has an N-terminal fragment of an anti-fibrin antibody (59DB) and a C-terminal thrombin-activatable low molecular weight single-chain urokinase plasminogen activator (scuPA-T). The scuPA-T portion was obtained by deletion of two amino acids (Phe157 and Lys 158) that make up the plasmin activation site from low molecular weight single chain urokinase-type plasminogen activator (scuPA).

5 Claims, 8 Drawing Sheets

59D8-scuPA

59D8-scuPA-T

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ACTCTGAGGC CCCGCATTAT TGGGGGAG        2 8

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Pro  Arg  Phe  Lys  Ile  Ile
    1                       5

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Pro  Arg  Ile  Ile
    1

THROMBIN-ACTIVATABLE PLASMINOGEN ACTIVATOR

FIELD OF THE INVENTION

This invention relates to plasminogen activators and methods of treatment of thrombosis. In particular, this invention relates to single chain urokinase and to chimeric immunoglobulin molecules incorporating a single chain urokinase region.

BACKGROUND OF THE INVENTION

Most myocardial infarctions are caused by coronary thrombosis. DeWood at al., *N. Eng. J. Med.*, 303, 897 (1983). The coronary thrombi that cause myocardial infarction can be lysed by thrombolytic agents, which significantly reduce mortality. ISIS-3 Collaborative Group, *Lancet*, 339, 753–70 (1992); Haber, et al., *Science*, 243, 51–6 (1989). However, currently available thrombolytic agents may also cause haemorrhagic strokes or other bleeding. ISIS, supra; Marder, V. J. and Sherry, S., *N. Engl. J. Med.* 318, 1512–20 (1988); Collen, D., *Am J. Cardiol.*, 69, 71A–81A (1992); Smitherman, T. C. *Mol. Biol. Med.*, 8, 207–18 (1991).

Plasmin and thrombin are both enzymes that affect coronary thrombi. Plasmin is a fibrinolytic enzyme, i.e., it lyses the fibrin present in a thrombus. Currently available thrombolytic agents activate the conversion of plasminogen to the fibrinolytic enzyme plasmin. Plasmin, however, also lyses fibrinogen, resulting in a bleeding diathesis.

Thrombin, on the other hand, initiates thrombus formation by cleavage of fibrinogen and activation of platelets. Mann, K. G. and Lundbald, R. L., *Hemostasis and Thrombosis: Basic Principles and Clinical Practice*, (Colman, R. W., et al., eds) 2nd ed., 148–161 (1987). It is produced locally around the site of injury and is absorbed into the thrombus by interacting with fibrin. Jackson, C. M., *Hemostasis and Thrombosis: Mechanism of Prothrombin Activation*, (Colman, R. W., et al., eds) 2nd ed.,148–161 (1987); Fenton, J. W., II, *Ann. N.Y. Acad. Sci.* 322, 468–495 (1981). Fibrin-bound thrombin is enzymatically active and is slowly released from a thrombus. Liu, C. Y. et al., *J. Biol. Chem.* 258, 10530–5 (1979). Therefore, the inventors have identified thrombin as a transient marker for a thrombus.

Single chain urokinase-type plasminogen activator (scuPA) is a zymogen. It can be activated by plasmin cleavage between Lys 158 and Ile 159, and inactivated by thrombin cleavage between Arg 156 and Phe 157. Lijnen, H. R. et al., *Semin. Throm. Hemostasis* 13, 152–9 (1987); Ichinose, A. et al., *J. Biol. Chem.* 261, 3486–9 (1986). Thus, scuPA-initiated plasma clot lysis is apt to be regulated by plasmin or thrombin around the thrombus.

Plasmin- or thrombin-resistant scuPA mutants have been produced to study plasmin activation or thrombin inactivation of scuPA. Nelles, L., Lijnen, H. R., Collen, D., and Holmes, W. E. *J. Biol. Chem.*, 262, 5682–9 (1987); Lijnen, R., et al. *Eur. J. Biochem.* 177, 575–82 (1988); Lijnen, R., et al. *Eur. J. Biochem.* 172, 185–8 (1988); Miyake, T.et al., *J. Biochem.* 104, 643–7 (1988); Eguchi, Y., et al., *J Biochem.* 108, 72–9 (1990). In order to increase scuPA's fibrin selectivity, chimeric plasminogen activators were constructed from an anti-fibrin antibody and low molecular weight scuPA. Both in vitro and in vivo, these activator constructs had better fibrin selectivity and higher potency than scuPA. Bode, C., et al., *Science.* 229, 765–7 (1985); Bode, C., et al., *J. Biol. Chem.* 262, 10819–23 (1987); Runge, M. S., et al., *Biochemistry*, 27, 1153–7 (1988). Collen, D., et al., *Fibrinolysis.* 3, 197–202 (1989); Dewerchin, M., et al., *Eur. J. Biochem.*, 185, 141–9 (1989); Holvoet, P., et al., *J. Biol. Chem.* 266, 19717–24 (1991); Runge, M. S., et al., *Proc. Natl. Acad. Sci. USA.* 88, 10337–41 (1991). A chimeric immunoglobulin molecule having an antibody variable region with an antigen binding site specific for fibrin and a fibrinolytic enzyme activity region has also been prepared by recombinant DNA techniques. European Patent Application 478,366, published 1 April 1992. The preferred embodiment in that application is r-scuPA(32)-59 D8.

The foregoing research has focused on ways to increase the fibrin selectivity of potential thrombolytic agents such as the scuPA mutants and conjugates. Due to the bleeding side-effect, however, the present inventors perceive a need for thrombolytic agents that distinguish between thrombi, which lead to myocardial infarction, and hemostatic plugs, which are mainly involved in prevention of bleeding. The present inventors hypothesized that plasminogen activators such as t-PA cannot distinguish fibrin epitopes on a pathogenic thrombus from those on a hemostatic plug. According to this hypothesis, thrombolytic agents lyse both thrombi and hemostatic plugs, causing bleeding during thrombolytic therapy. See Sherry, *Mod. Conc. Cardiovas. Disease.* 60, 25–30 (1991).

SUMMARY OF THE INVENTION

In accordance with the present invention, the present inventors designed a chimeric immunoglobulin molecule comprising (a) an antibody variable region with an antigen binding site specific for fibrin, covalently linked to (b) a single chain urokinase region having a thrombin activatable site but not a plasmin activatable site. In a preferred embodiment, the antibody variable region of the chimeric immunoglobulin molecule is a high-affinity anti-fibrin antibody fragment (Fab), with an antibody fragment from 59D8 most preferred.

Also in accordance with the present invention are nucleic acid molecules having sequences coding for the aforementioned chimeric immunoglobulin molecule, expression vectors having that sequence, and host cells transformed by such vectors. This invention also includes a method for preparing the chimeric immunoglobulin molecule in which such host cells are grown under conditions that allow expression of the nucleic acid sequence of the vector, after which the immunoglobulin molecule may be purified.

Further in accordance with the present invention is a pharmaceutical composition comprising the aforementioned chimeric immunoglobulin molecule and a pharmaceutically acceptable carrier. The present invention further includes a method of lysing a thrombus in a mammalian subject, which comprises administering to the subject an effective amount of the chimeric immunoglobulin molecule. Further still, the present invention includes a method of detecting a thrombus in a mammalian subject, which comprises administering the chimeric immunoglobulin molecule having a detectable marker and then detecting the presence of the marker.

59D8-scuPA contains a genomic heavy-chain variable region from fibrin-specific monoclonal antibody 59D8, the cloned genomic constant region of mouse ,2b[CH1 and H (hinge)], and the coding region from a genomic clone of scuPA (containing exons VII through XI).

Figure 2:
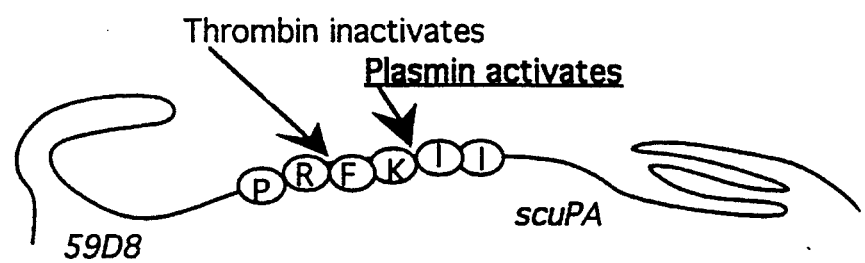
Figure 2:
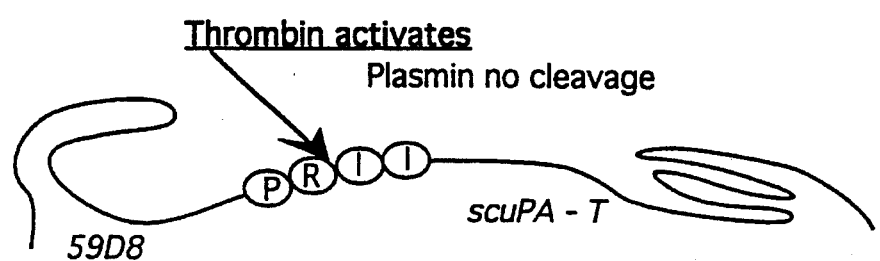

FIG. 2. Schematic drawing of 59D8-scuPA and 59D8-scuPA-T

Thrombin and plasmin cleavage sites are represented by arrows. The first recited amino acid sequence of -Pro-Arg-Phe-Lys-Ile-Ile- has the sequence indentification of SEQ. ID. No. 2, and the second recited amino acid sequence of -Pro-Arg-Ile-Ile- has the sequence identification of SEQ. ID. No. 3.

FIG. 3. SDS-PAGE and Immunoblotting of 59D8-scuPA and 59D8-scuPA-T

Part A shows a 12% sodium dodecyl sulfate polyacrylamide gel electrophoresis (SDS-PAGE). Prestained standards appear in lane 1. The samples were run under nonreducing conditions in lanes 2 and 3, and under reducing conditions using β-mercaptoethanol in lanes 4 to 7. 59D8 antibody was run in lane 6 and low molecular weight urokinase in lane 7. In part B, the gel was immunoblotted using goat anti-human urokinase (urokinase was run in lane 6). In part C, the gel was immunoblotted using goat anti-mouse immunoglobulin G (IgG). 59D8 was run in lane 6.

Figure 4:
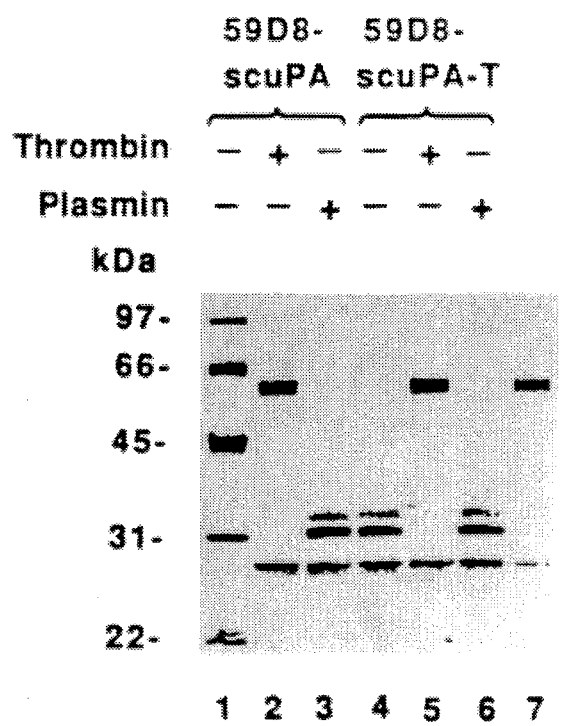

FIG. 4. SDS-PAGE of thrombin- or plasmin-digested 59D8-scuPA and 59D8-scuPA-T

This figure shows a 12% reducing gel of samples treated with N-glycanase.

Figure 5:
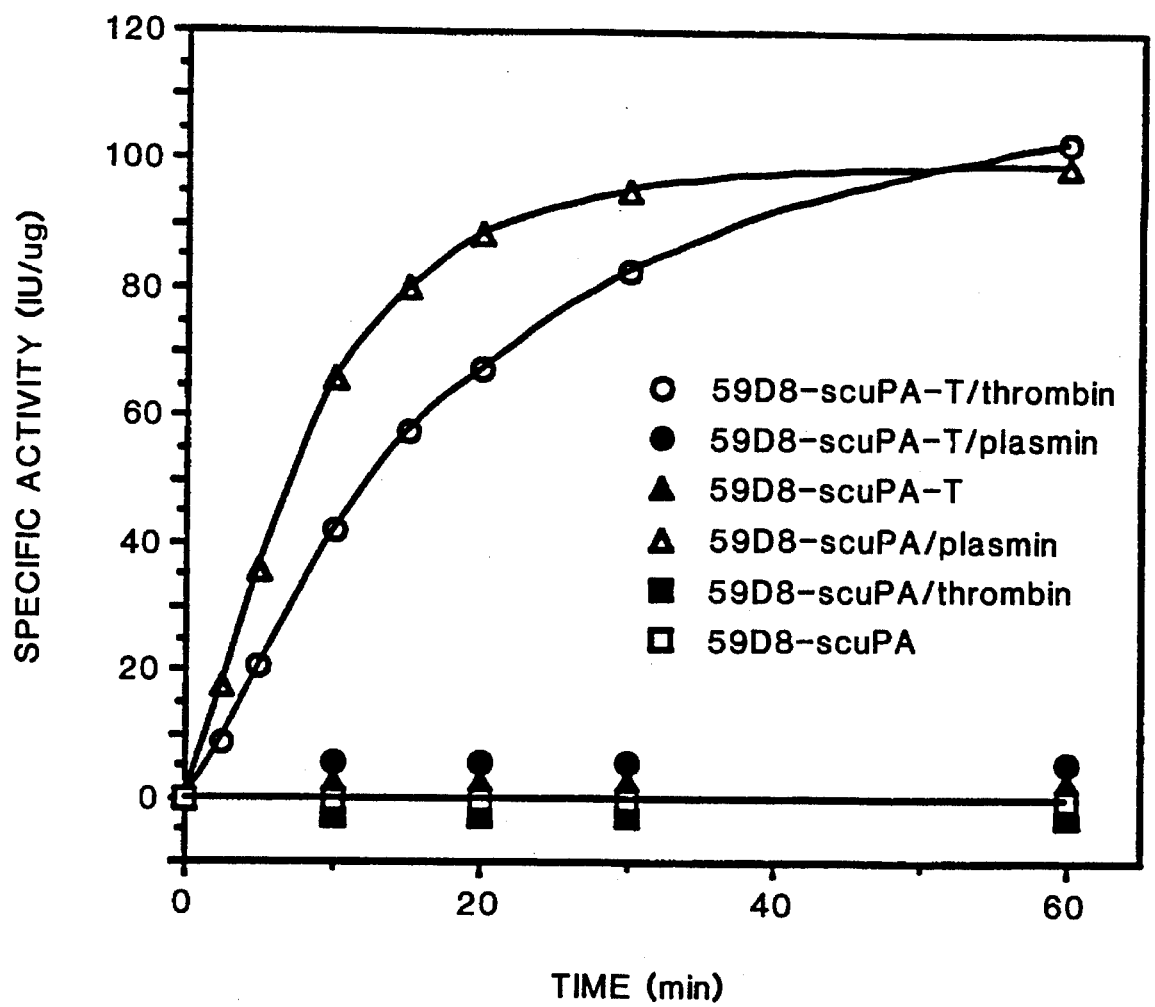

FIG. 5. Treatment of 59D8-scuPA and 59D8-scuPA-T with Plasmin and Thrombin

Generated urokinase-like amidolytic activity is expressed in IU/µu-PA. A final concentration of 5 nM plasmin and thrombin was used for 59D8-scuPA (150 nM). A final concentration of 15 nM plasmin and thrombin was used for 59D8-scuPA-T (150 nM).

Figure 6:
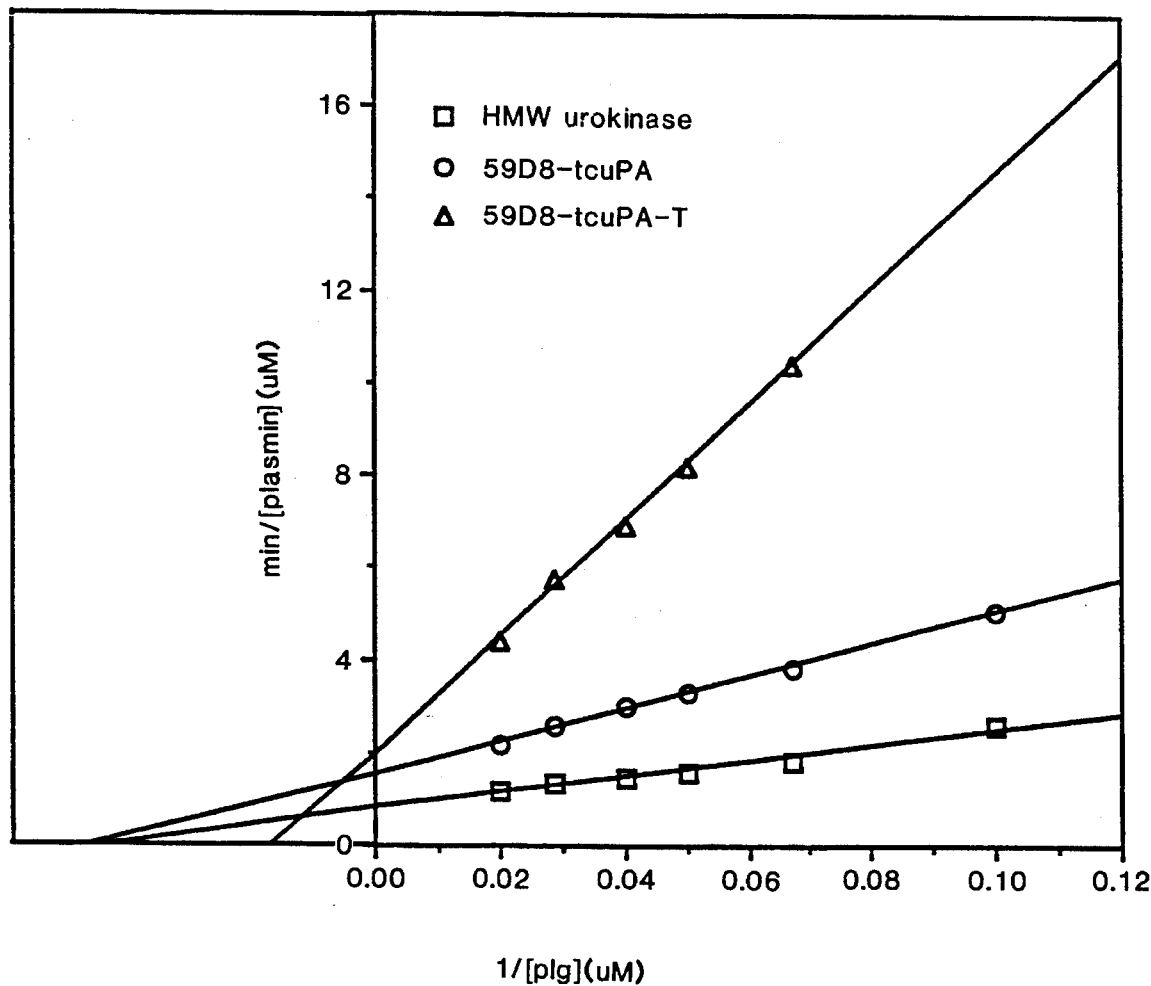

FIG. 6. Lineweaver-Burk Plot for the Activation of Plasminogen (Plg)

Wild type scuPA cleaved by plasmin is referred to herein as "tcuPA". 5 nM of 59D8-tcuPA, 59D8-tcuPA-T, and commercially obtained high molecular weight urokinase was treated with plasminogen over a range of 10 to 50 µM The data represent the average of four experiments.

FIG. 7. Lysis of $^{125}$I-Fibrin Labeled Human Plasma Clots Immersed in Human Plasma For part A, 1 µg/mL of plasminogen activator was present in the forming clot. In the control, there was no plasminogen activator present in the forming clot. For part B, 3 µg/mL plasminogen activator was added to the plasma. In the control, there was no plasminogen activator present in the plasma milieu.

FIG. 8. Titration Curves of Lysis of $^{125}$I-Fibrin Labeled Human Plasma Clots in Human Plasma Heparin was added at a concentration of 50 units/mL where indicated. Part A shows heparin addition with 59D8-scuPA; part B, with 59D8-scuPA-T.

DETAILED DESCRIPTION OF THE INVENTION

Definition of Terms

The following definitions apply to the terms as they appear throughout this specification, unless otherwise limited in specific instances.

The term "scuPA" refers to single chain urokinase-type plasminogen activator. It exists in two forms—high molecular weight and low molecular weight. High molecular weight scuPA has a molecular weight of about 54 kDa and comprises a EGF domain, a kringle domain, a thrombin inactivation site, a plasmin activation site and a protease domain. Low molecular weight scuPA has a molecular weight of about 34 kDa and is a degradation product of high molecular weight scuPA that lacks the EGF and kringle domain but has the rest of the domains. Such single chain urokinase regions are described, for example, in Bachmann, F., *Hemostasis and Thrombosis: Basic Principles and Clinical Practice* (Colman, R. W., et al., eds.) 2nd ed., pp. 318–39 (1987); Stump et al,, *J. Biol. Chem.*, 261 17120 (1986); Nelles et al., *J Biol. Chem.*, 262, 10855 (1987). The domains needed to maintain thrombolytic activity may be determined by cloning, subcloning, expression and screening procedures well known to those having ordinary skill in the art. The term "single chain urokinase region" comprises sequences based on both the low and high molecular weight forms of scuPA, although the low molecular weight form is preferred.

The term "scuPA-T" refers to a scuPA mutant made by deleting the two amino acids phenylalanine (157)-lysine (158) located between thrombin and plasmin cleavage sites, as shown in FIG. 2.

The term "59D8" refers to the monoclonal antibody fragment prepared by the procedures described in Quertermous et al., *J. Immunol.*, 2687–90 (1987).

The term "fibrin-specific" as used to describe antibodies refers to antibodies raised against fibrin. Such antibodies have been described, for example, in Hui et al., *Science*, 222, 1129 (1983); U.S. Pat. No. 4,927,916, issued May 22, 1990; U.S. Pat. No. 4,916,070, issued Apr. 10, 1990; Kudryk, et al., *Mol. Immunol.*, 21, 89 (1984); European Patent Application 146, 050, published 26 June 1985; and Australian Patent Application AV-A-25387/84.

Process of Preparation

In order to design a novel plasminogen activator that is able to distinguish new from old clots, a surface marker on a new clot is required. The inventors identified active fibrin-bound thrombin as such a marker based on certain known characteristics of thrombin: (1) thrombin is produced locally around the injury site, (2) thrombin is located around a thrombus, (3) thrombin tends to leach out of a fibrin clot during extensive washing, and (4) prolonged exposure of surface-bound thrombin in circulating plasma may result in inactivation by plasma protease inhibitors.

The regions making up the chimeric molecule of the present invention may be prepared as follows.

Single Chain Urokinase Region

The single chain urokinase region may be prepared by recombinant nucleic acid methods. See, for example, the recombinant DNA methods of Nelles et al., *J. Biol. Chem.*, 262, 10855 (1987).

The DNA sequence may be derived from a variety of sources, including genomic DNA, subgenomic DNA, cDNA, synthetic DNA, and combinations thereof. Genomic and cDNA may be obtained in a number of ways. Cells coding for the desired sequence may be isolated, the genomic DNA fragmented (e.g., by treatment with one or more restriction endonucleases), and the resulting fragments cloned, identified with a probe complementary to the desired sequence, and screened for the presence of a sequence coding for fibrin recognition or for thrombolytic activity.

The cDNA may be cloned and the resulting clone screened with a probe for the desired region. Upon isolation of the desired clone, the cDNA may be manipulated in substantially the same manner as the genomic DNA.

To provide for thrombin activation only, the plasmin cleavage site from a single chain urokinase region is deleted while the thrombin cleavage site remains. This deletion may take place at the nucleic acid level, in which the nucleotides encoding the plasmin cleavage site are deleted, or at the protein level. For both nucleic acids and proteins, the necessary procedures are well known to those having ordinary skill in the art. A preferred procedure is site-directed mutagenesis, in which a primer lacking the sequence coding for the plasmin cleavage site is used in a T7 DNA polymerase reaction or a polymerase chain reaction (PCR).

Fibrin-Specific Antibody Region

In preparing the chimeric immunoglobulin molecule of the present invention, the entire fibrin-specific antibody may be cloned. In order to reduce the size of the molecule and to reduce antigenicity, it is preferred to use only that region of the antibody that will bind to fibrin.

The variable and constant regions of the fibrin-specific antibody used may be derived from a mammalian source, with a human source preferred. The variable and constant regions may, however, be derived from separate sources; for example, the variable region may be derived from a non-human mammalian source and the constant regions from a human source to reduce antigenicity. Principles and procedures used to isolate such regions are well known in the art. See, for example, European Patent Application 478, 366, published Apr. 1, 1990.

For the variable region of the fibrin-specific antibody, the rearranged heavy chain coding DNA may include V, D, and J regions. The rearranged germlin light chain coding DNA may include the V and J regions. Upon identification of the cloned fragment containing the sequence for the fibrin-specific binding site, that fragment may be further manipulated; for example, to remove superfluous DNA (including all or part of any introns present) or to modify one or both termini.

Control Regions

To express the chimeric immunoglobulin molecule, transcriptional and translational signals recognized by an appropriate host are necessary.

The promoter region from genomic DNA may be obtained in association with the DNA sequence for the fibrin-specific antibody region or the single chain urokinase region. To the extent that the host cells recognize the transcriptional regulatory and translational initiation signals associated with the variable region, the 5' region adjacent to the coding sequence may be retained and employed for transcriptional and translational regulation. This region typically will include those sequences involved with initiation of transcription and translation, such as the TATA box, capping sequence, CAAT sequence, and the like. Typically, this region will be at least about 150 base pairs long, more typically about 200 bp and rarely exceeding about 1 to 2 kb.

The non-coding 3' region may be retained, as well, especially for its transcriptional termination regulatory sequences, such as the stop signal and polyadenylated region. In addition, the non-coding 3' region may also contain an enhancer in immunoglobulin genes. Where the transcriptional termination signals are not satisfactorily functional in the host cell, then a functional 3' region from a different gene may be substituted. In this method, the choice of the substituted 3' region would depend upon the cell system chosen for expression.

A wide variety of transcriptional and translational regulatory sequences may be employed, depending upon the nature of the host. The transcriptional and translational regulatory sequences may be derived from viral sources (e.g., adenovirus, *bovine papilloma* virus, Simian virus, and the like) where the regulatory signals are derived from a gene that has a high level of expression in the host. Alternatively, promoters from mammalian expression products (e.g., actin, collagen, myosin, and the like) may be employed. Transcriptional initiation regulatory signals may be selected that allow for repression or activation, so that expression of the genes can be modulated. One such controllable modulation technique is the use of regulatory signals that are temperature-sensitive, so that expression can be repressed or initiated by changing the temperature. Another controllable modulation technique is the use of regulatory signals that are sensitive to certain chemicals.

Formation of the Chimeric Construct

DNA fragments may be ligated in accordance with conventional techniques known in the art. Such techniques include use of restriction enzymes to digest DNA fragments, DNA polymerases and nucleotides to fill in sticky ends to form blunt ends, alkaline phosphatase to avoid undesired ligations, and ligases to join fragments.

The constructs for the fibrin-specific antibody and single chain urokinase regions may be joined together to form a single DNA segment or may be maintained as separate segments by themselves. The constructs may be introduced into a cell by transformation in conjunction with a gene allowing for selection where the construct will become integrated into the host genome. Usually, the construct will be part of a vector having a replication system recognized by the host cell.

Expression Vectors

Expression vehicles for production of the molecules of the invention include plasmids or other vectors. In general, such vectors contain control sequences that allow expression in various types of hosts, including but not limited to prokaryotes, yeasts, fungi, plants and higher eukaryotes. Suitable expression vectors containing the desired coding and control sequences may be constructed using recombinant DNA techniques known in the art, many of which are described in Sambrook, et al., *Molecular Cloning: A Laboratory Manual*, Second Edition, Cold Spring Harbor Laboratory, Cold Spring Habor, N.Y. (1989).

An expression vector as contemplated by the present invention is at least capable of directing the replication, and preferably the expression, of the nucleic acids of the present invention. One class of vectors utilizes DNA elements that provide autonomously replicating extrachromosomal plasmids derived from animal viruses (e.g., *bovine papilloma* virus, *polyomavirus, adenovirus*, or SV40 virus). A second class of vectors relies upon the integration of the desired gene sequences into the host cell chromosome.

Expression vectors useful in the present invention include sequences that control the replication and expression of the subject DNA sequence. Typically, the expression vector contains an origin of replication, a promoter located 5' to (i.e., upstream of) the DNA sequence to be expressed, and a transcription termination sequence. Suitable origins of replication include, for example, the Col E1, the SV40 viral and the M13 orgins of replication. Suitable termination sequences include, for example, the bovine growth hormone, SV40, lac Z and the *Autographa californica* multiple nuclear polyhedrosis virus (AcMNPV) polyhedral polyadenylation signals. Suitable promoters include, for example, the immunoglobulin H chain promoter, the cytomegalovirus promoter, the lac Z promoter, the gal 10 promoter and the AcMNPV polyhedral promoter.

The expression vectors may also include other regulatory sequences for optimal expression of the desired product. Such sequences include stability leader sequences, which provide for stability of the expression product; secretory leader sequences, which provide for secretion of the expression product; enhancers, which upregulate the expression of the DNA sequence; and restriction enzyme recognition sequences, which provide sites for cleavage by restriction endonucleases. All of these materials are known in the art and are commercially available. See, for example, Okayama, *Mol. Cell. Biol.*, 3 280 (1983).

A suitable expression vector may also include marking sequences, which allow phenotypic selection of transformed host cells. Such a marker may provide prototrophy to an auxotrophic host, biocide resistance (e.g., antibiotic resistance) and the like. The selectable marker gene can either be directly linked to the DNA gene sequences to be expressed, or introduced into the same cell by co-transfection. Examples of selectable markers include neomycin, ampicillin, hygromycin resistance and the like.

Host Cells

The present invention additionally concerns host cells containing an expression vector or vectors that comprise a DNA sequence coding for the chimeric immunoglobulin molecule. In a preferred embodiment, the expression vector for the chimeric molecule only has the sequence for the heavy chain of the fibrin-specific antibody and is used with host cells that provide the light chain. Alternatively, the expression vector for the chimeric molecule could be co-transfected with an expression vector for the light chain of the fibrin-specific antibody.

The preferred hosts are mammalian cells, grown in vitro in tissue culture, or in animals. Mammalian cells may provide post-translational modification to immunoglobulin protein molecules, including correct folding or glycosylation at correct sites. Mammalian cells that may be useful as hosts include cells of fibroblast origin (e.g., VERO or CHO-K1) or lymphoid origin (e.g., SP2/0-AG14, or P3x63Sg8) or derivatives thereof. Preferred mammalian host cells include 5P2/0 and J558L. The host cells of Schnee, et al., *Proc. Natl. Acad. Sci. USA.* 84, 6904–8 (1987) are most preferred.

Immortalized cells, particularly myeloma or lymphoma cells, are also suitable host cells. These cells may be grown in an appropriate nutrient medium in culture flasks or injected into a synergenic host (e.g., mouse or rat) or an immunodeficient host or host site (e.g., nude mouse or hamster pouch). In particular, the cells may be introduced into the abdominal cavity for production of ascites fluid and harvesting of the chimeric molecule. Alternatively, the cells may be injected subcutaneously and the antibodies harvested from the blood of the host. The cells may be used in the same manner as the hybridoma cells. See Diamond et al., *N. Eng. J. Med.*, 344 (1981); *Monoclonal Antibodies: Hybridomas-A New Dimension in Biologic Analysis* (Kennatt, et al., eds.) Plenum (1980).

When using co-transfection with a light chain expression vector, many different prokaryotic and eukaryotic host cells may be employed. Suitable prokaryotic host cells include, for example, *E. coli* strains HB101, DH5a, XL1 Blue, Y1090 and JM101. Suitable eukaryotic host cells include, for example, *Spodoptera frugiperda* insect cells, COS-7 cells, human fibroblasts, and *Saccharomyces cerevisiae* cells.

Expression of the Chimeric Immunoglobulin Molecule

Expression vectors may be introduced into host cells by various methods known in the art. For example, transfection of host cells with expression vectors can be carried out by the calcium phosphate precipitation method. However, other methods for introducing expression vectors into host cells, for example, electroporation, liposomal fusion, nuclear injection, and viral or phage infection can also be employed.

Host cells containing an expression vector that contains a DNA sequence coding for the chimeric immunoglobulin molecule may be identified by one or more of the following six general approaches: (a) DNA—DNA or RNA-DNA hybridization; (b) the presence or absence of marker gene functions; (c) assessment of the level of transcription by measuring production of mRNA transcripts encoding the chimeric immunoglobulin molecule in the host cell; (d) detection of the gene product immunologically; (e) enzyme assay; and (f) PCR.

In the first approach, the presence of a DNA sequence coding for the chimeric immunoglobulin molecule can be detected by DNA—DNA or RNA-DNA hybridization using probes complementary to the DNA sequence.

In the second approach, the recombinant expression vector/host system can be identified and selected based upon the presence or absence of certain marker gene functions (e.g., thymidine kinase activity, resistance to antibiotics, etc.). A marker gene can be placed in the same plasmid as the DNA sequence coding for the chimeric immunoglobulin molecule under the regulation of the same or a different promoter used to regulate the coding sequence. Expression of the marker gene indicates expression of the DNA sequence coding for the chimeric immunoglobulin molecule.

In the third approach, the production of mRNA transcripts encoding the chimeric immunoglobulin molecule can be assessed by hybridization assays. For example, polyadenylated RNA can be isolated and analyzed by Northern blotting or a nuclease protection assay using a probe complementary to the RNA sequence. Alternatively, the total RNA of the host cell may be extracted and assayed for hybridization to such probes.

In the fourth approach, the expression of the chimeric immunoglobulin molecule can be assessed immunologically, for example, by immunoblotting with antibody to either the chimeric immunoglobulin molecule, the single chain urokinase region, or the antibody variable region (Western blotting). Alternatively, this technique could be carried out with the known epitope of the antibody variable region.

In the fifth approach, expression of the chimeric immunoglobulin molecule can be measured by assaying for its activity. For example, the clot lysis assay described hereinbelow may be employed.

In the sixth approach, oligonucleotide primers homologous to sequences present in the expression system (i.e., expression vector sequences or the chimeric immunoglobulin molecule sequences) are used in a PCR to produce a DNA fragment of predicted length, indicating incorporation of the expression system in the host cell.

The expression vectors and DNA molecules of the present invention may also be sequenced. Various sequencing methods are known in the art. See, for example, the dideoxy chain termination method described in Sanger et al., *Proc. Natl. Acad. Sci. USA* 74, 5463–7 (1977), and the Maxam-Gilbert method described in *Proc. Natl. Acad. Sci. USA* 74, 560–4 (1977).

Once an expression vector has been introduced into an appropriate host cell, the host cell may be cultured under conditions permitting expression of large amounts of the desired polypeptide, in this case the chimeric immunoglobulin molecule. Expression of the gene or genes encoded by the vector results in assembly to form the chimeric immunoglobulin molecule.

The chimeric immunoglobulin molecule may be isolated and purified in accordance with conventional conditions, such as extraction, precipitation, chromatography, affinity chromatography, electrophoresis, and the like. The preferred method is affinity chromatography with either the amino terminal heptapeptide of the fibrin β chain, which binds to the antifibrin site, or benzamidine, which binds to the plasminogen activator catalytic site.

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

Use and Utility

The chimeric immunoglobulin molecule of the present invention is a thrombolytic agent and so will be useful in all ways known for thrombolytic agents. For example, it is useful in treatment of a patient following acute myocardial infarction, stroke, and deep vein thrombosis. The chimeric immunoglobulin molecule is also an anti-thrombotic agent useful, for example, to prevent rethrombosis from occurring after thrombolytic therapy and angioplasty surgery.

For such therapeutic applications, the chimeric immunoglobulin molecule is administered to a patient and becomes localized to the site of a thrombus through the fibrin-specific binding site of the chimeric molecule. The chimeric molecule is activated by thrombin present at the site of the newly forming clot. The thrombus is lysed by the enzymatic activity of the activated urokinase region of the chimeric immunoglobulin molecule.

One advantage of this chimeric immunoglobulin molecule is that it preferentially lyses thrombi rather than hemostatic plugs, thus avoiding the bleeding side-effect associated with other known thrombolytic agents. Another advantage is that, unlike tPA, the subject chimeric immunoglobulin molecule should be stable in human plasma.

The chimeric immunoglobulin molecule of the present invention may also be used in immunodiagnostic applications, including immunodiagnosis. In this application, the chimeric molecule is detectably labeled, preferably with a radionuclide. The radionuclide must be of the type of decay that is detectable by a given type of instrument. Further, the radionuclide for in vivo diagnosis should have a half-life long enough that it is still detectable at the time of maximum uptake, but short enough that after diagnosis unwanted radiation does not remain in the patient. Coupling of the radionuclides to the chimeric molecule is known in the art and is often accomplished either directly or indirectly using an intermediary functional group. Examples of radioisotopes useful for diagnosis are $^{99}$Tc, $^{123}$I, $^{131}$I, $^{97}$Ru, $^{67}$Cu, $^{67}$Ga, $^{68}$Ga, $^{72}$As, $^{89}$Zr, and $^{201}$Ti. Paramagnetic isotopes for purposes of diagnosis can also be used according to the methods of this invention. Examples of elements that are particularly useful for Magnetic Resonance Energy techniques include $^{157}$Gd, $^{55}$Mn, $^{162}$Dy, $^{52}$Cr, and $^{56}$Fe.

The chimeric immunoglobulin molecule can further be part of a pharmaceutical composition that also comprises a pharmaceutically acceptable carrier. These carriers are well known in the art and can include aqueous or solvent emulsions and suspensions, including saline and buffered media. Such formulations are well known in the pharmaceutical art. See, for example, *Remington's Pharmaceutical Sciences* (16th Ed. 1980).

The dosage ranges for administration of the chimeric immunoglobulin molecules are those that are large enough to detect the presence of thrombi. The dosage will vary with the age, condition, sex, and extent of disease in the patient. Counterindications can include hypersensitivity and other variables and can be adjusted by the individual physician. Dosage can range from 0.01 to 500 mg/kg of body weight, preferably 0.01 to 200 mg/kg. The chimeric immunoglobulin molecule can be administered parenterally by injection or by gradual perfusion over time. They can also be administered intravenously, intraperitoneally, intramuscularly, or subcutaneously.

Preferred Embodiments

In the preferred embodiment, two amino acids are deleted from scuPA, Phe157 and Lys158, to a create a mutant with the sequence Arg(154)-Pro-Arg-Ile-Ile(158) around the native plasmin/thrombin sites (scuPA-T). Because the native plasmin site at Lys 158 has been removed, the mutant sequence can only be cleaved by thrombin and the new N-terminal amino acid is isoleucine (See FIG. 5 for 59D8-scuPA-T). As expected, the protein containing the mutant sequence cleaved by thrombin (59D8-tcuPA-T) is capable of activating plasminogen, although it is not as active as the wild type scuPA cleaved by plasmin (59D8-tcuPA; see FIG. 6). In vitro plasma clot lysis assays showed that 59D8-scuPA-T lysed thrombin induced plasma clots and that lysis was quenched by heparin (FIG. 8B), further indicating that scuPA-T is a thrombin-activatable plasminogen activator. The 59D8-scuPA and wild type scuPA are both activated by plasmin, and therefore lysed thrombin-containing and thrombin-depleted clots equally well.

Clot lysis experiments also revealed that 59D8-scuPA-T was much better at dissolving a clot than 59D8-scuPA or high molecular weight scuPA when it was present within the forming clot. Since there was more active thrombin present in the forming clot as compared to the plasma, they could activate 59D8-scuPA-T and inactivate 59D8-scuPA and high molecular weight scuPA. This result suggests that 59D8-scuPA-T can act as an antithrombotic agent working at the site of clots that are being initially formed.

The invention will now be further described by the following working examples, which are preferred embodiments of the invention. These examples are illustrative rather than limiting. Unless otherwise indicated, all temperatures are in degrees Celsius (°C.).

EXAMPLE 1.

Construction of 59D8-Scupa-T Chimeric Molecule

Construction of a Thrombin-Activatable Low Molecular Weight scuPA

A 3.0 kb human genomic DNA fragment encoding the gene for scuPA, including exons 7 to 11, was subcloned into the XhoI/XbaI site of a pBluescriptII KS vector (Promega). Phagemid mutagenesis was carried out according to the manufacturer's protocol (BioRad). The oligomer used for mutagenesis was a 28-mer having the following sequence (SEQ. ID. NO. 1), listed here 5' to 3':

ACT CTG ASS CCC CGC ATT ATT GGG GGA G'

SEQ. ID. NO. 1 corresponds to the DNA sequence encoding amino acids 152 to 163 of scuPA except the deletion of 6 nucleotides that encode amino acids 157 (Phe) and 158 (Lys). The nucleotide sequence of the mutant was verified by dideoxy nucleotide sequencing analysis using T7 Sequenase according to the manufacture's protocol (United States Biochemical Corp.).

Construction and Expression of 59D8-scuPA and 59D8-scuPA-T

The 3.0 kb XhoI/SalI fragment containing human genomic DNA encoding for low molecular weight scuPA (scuPA) or for the deletion mutant of scuPA (scuPA-T) were cloned into the XhoI/SalI site of the expression vector p220RX. The vector p220RX was derived from expression vector pSVUKG(Ig) by deleting CH2 domain with XhoI digestion of the vector. Runge, et al., *Proc. Natl. Acad. Sci. USA.* 88, 10337-41 (1991). Constructs having inserts in the correct orientation were screened by XhoI restriction mapping. The final expression vectors 59D8-scuPA (shown in FIG. 1) and 59D8-scuPA-T were linearized by SalI digestion and 40 µg of each was transformed into a 59D8 light-chain producing hybridoma cell line by electroporation as previously described. Schnee et al., *Proc. Natl. Acad. Sci. USA.* 84, 6904-8 (1987).

The transformed cells were grown in selection media described previously Id. Colonies growing in the selection media were screened for the production of chimeric plasminogen activator by incubating 50 µL of the culture medium in a 96-well microtiter plate coated with β-7 peptide (the heptapeptide epitope for antibody 59D8) for two hours. Bound protein was then detected by peroxidase conjugated goat anti-mouse IgG or by anti-human urokinase and then by peroxidase conjugated rabbit anti-goat antibody. Runge, supra.

Cell lines producing 59D8-scuPA and 59D8-scuPA-T were grown in a Cellquad hollow fiber bioreactor (Cellco). Approximately 1×10⁷ cells were inoculated into a polypropylene bioreactor cartridge (Cellco) with a capillary pore size of 0.5 microns and an extra-capillary space volume of 7.0 mL. The extra-capillary space (ECS) medium and the perfusion medium consisted of AIM-V serum-free medium (Gibco) supplemented with 300 IU/mL Aprotinin (American Diagnostica) and 10 µg/mL Soybean trypsin inhibitor (Sigma). Two weeks after inoculation, chimeric proteins were harvested every one or two days from the perfusion medium reservoir bottle.

Figure 1:
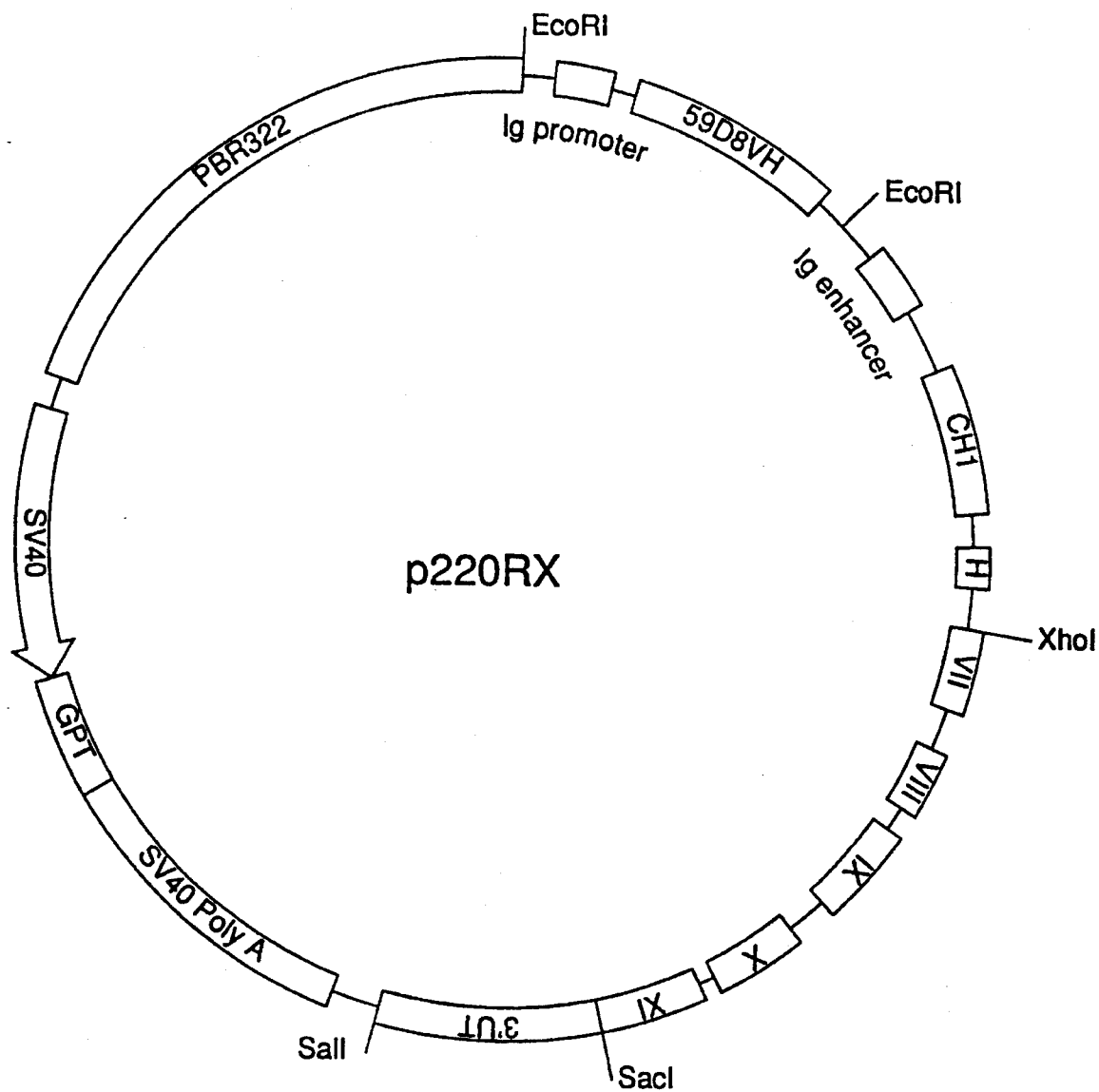
FIG. 1. Expression Plasmid for 59D8-scuPA

FIG. 1 shows the expression vector used in transfecting a 59D8 light chain-producing mouse hybridoma cell line. 59D8-scuPA-T was constructed and expressed in the same manner, except that the two amino acids between the plasmin and thrombin cleavage sites (Phe 157 and Lys158) were removed by site-directed mutagenesis (FIG. 2). The schematic structure of 59D8-scuPA and 59D8-scuPAT are shown in FIG. 3.

Purification of 59D8-scuPA and 59D8-scuPA-T

Chimeric plasminogen activators were purified from the perfused bioreactor medium by affinity chromatography on a β-7/sepharose matrix prepared as previously described. Runge, supra. β-7 peptide is the epitope on fibrin monomers that the 59D8 antibody recognizes. Chimeric proteins bound to the column were eluted with 0.2M Glycine pH 3.5 and the eluted proteins were immediately neutralized with the addition of ⅕ volume 1M Tris-HCl pH 7.8. The protein solutions were then concentrated using Centriprep 30 concentrators (Amicon). The pooled, purified samples were passed over the affinity column a second time for further purification.

The concentrations in solution of 59D8-scuPA and 59D8-scuPA-T were determined by the DC protein assay as described by the manufacturer (BioRad).

SDS-PAGE and Western Blotting

The purity and intactness of the affinity-purified chimeric plasminogen activators were checked by SOS-PAGE under reducing (using β-mercaptoethanol) and non-reducing conditions. The proteins were visualized by either staining with Coomassie brilliant blue R or by transferring by electrophoresis to a PVDF membrane (Westran) for Western blotting. Alkaline phosphatase-conjugated goat anti-mouse IgG (Kirkegaard & Perry Laboratories) was used to detect Fab epitopes. Goat anti-human urokinase (American Diagnostica) and alkaline phosphatase-conjugated rabbit anti-goat IgG (Kirkegaard & Perry Laboratories) was used to detect scuPA epitopes.

Figure 3A:
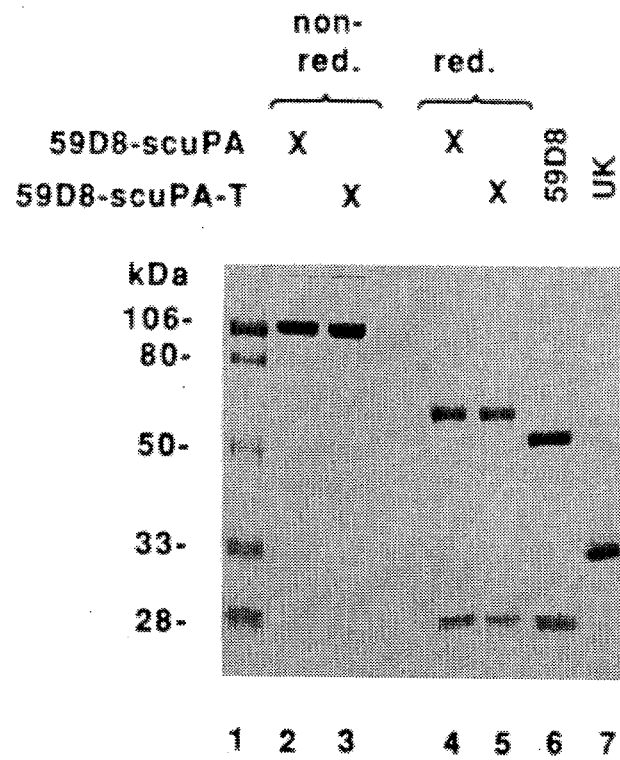
Figure 3B:
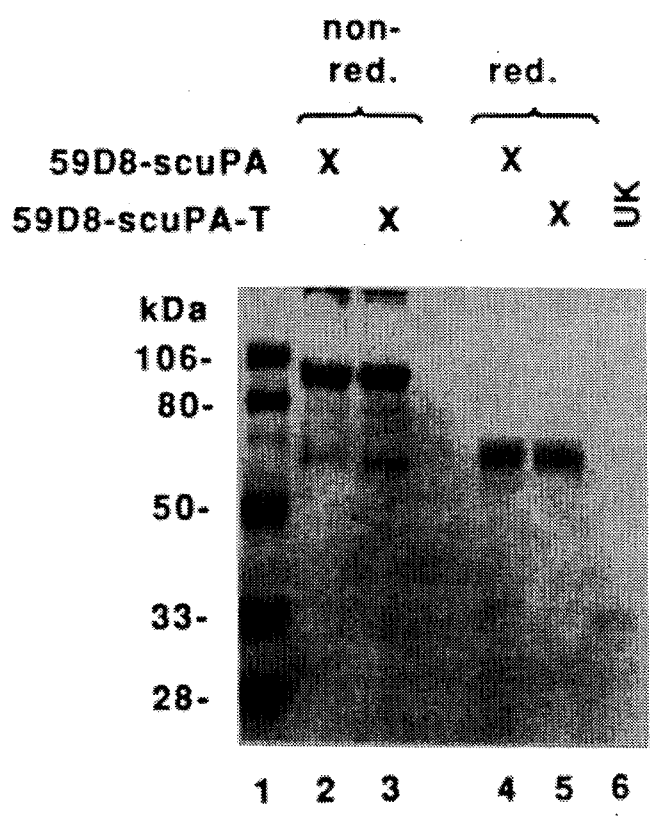
Figure 3C:
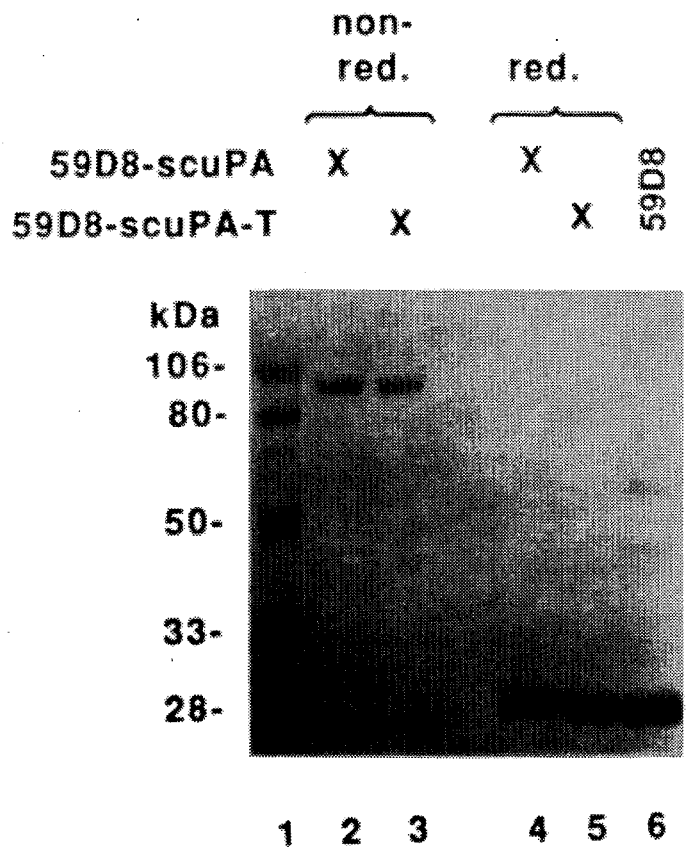

The Coomassie blue-stained gel of the proteins show one band at 91 kDa under non-reducing conditions and two bands of 27 kDa and 64 kDa under reducing conditions (FIG. 3A). The 91 kDa band can be detected by both goat anti-mouse IgG and goat anti-human urokinase antibodies in western blot analysis, while the 64 kDa band can only be detected by goat anti-human urokinase and the 27 kDa band only by goat anti-mouse IgG (FIG. 3B and 3C). This result shows that the 91 kDa band is the chimeric protein consisting of the 59D8Fd and scuPA fusion protein disulfide linked to the 59D8 L chain (27 kDa). The 64 kDa band is the fusion of 59D8Fd (31 kDa) and scuPA(33 kDa), and the 27 kDa band is the light chain of 59D8 (27 kDa). The 64 kDa band cannot be detected by goat anti-mouse IgG because this antibody cannot recognize the reduced form of 59D8Fd (data not shown).

Amino-Terminal Sequence Analysis

Intact, thrombin-cleaved (Bovine, Armour Pharmaceutical) or plasmin-cleaved (American Diagnostica) chimeric protein was subjected to amino-terminal sequence analysis using a gas-phase sequencer (ABI). Amino-terminal sequencing revealed that the plasmin cleavage occurred at Lys158 of scuPA and the thrombin cleavage occurred at Arg156 (data not shown). Only thrombin, however, was capable of digesting 59D8-scuPA-T with the cleavage occurring between Arg156 and Ile157 (see FIG. 2).

EXAMPLE 2

Demonstration of Clot Lysis Activity

Plasmin and Thrombin Treatment of 59D8-scuPA and 59D8-scuPA-T

59D8-scuPA or 59D8-scuPA-T (150 nM final concentration) in TNT buffer (0.05M Tris-HCl, pH 7.4, 0.038 M NaCl, 0.01% Tween 80) was treated at 37° C. with plasmin (5 nM final concentration) or thrombin (15 nM final concentration). At timed intervals (0–60 minutes), the urokinase-like amidolytic activity was measured using the chromogenic substrate s-2444 (0.3 mM final concentration; Kabi Pharmacia) after stopping the reaction with either aprotinin (5000 KIU/mL final concentration) for the plasmin digestions or hirudin (1 U/mL; Calbiochem) for the thrombin digestions. Urokinase activity was expressed in International units (IU) by comparison with the International Standard (87/594; WHO International Laboratory for Biological Standards).

Stock solutions of 59D8-tcuPA and 59D8-tcuPA-T were obtained by treating 59D8-scuPA (10 mM final concentration) with plasmin (2 mol/100 mol) and 59D8-scuPA-T (10 mM final concentration) with thrombin (1 NIHU/2 nmol) for 30 minutes at 37° C. Plasmin and thrombin were removed by passing the samples over the β-7/sepharose column. The conversion of urokinase from the one-chain to the two-chain form was monitored by SDS-PAGE on 12% gels after reduction with β-mercaptoethanol.

Both plasmin and thrombin were able to digest 59D8-scuPA, as shown on the SDS-PAGE in FIG. 4. The 64 kDa band was cleaved to yield 31 and 33 kDa bands. Amino-terminal sequencing revealed that the plasmin cleavage occurred at Lys158 of scuPA and the thrombin cleavage occurred at Arg156 (data not shown). Only thrombin, however, was capable of digesting 59D8-scuPA-T with the cleavage occurring between Arg156 and Ile157 (see FIG. 2).

Plasmin caused a time-dependent conversion of 59D8-scuPA to its two-chain derivative, and the result was the same for thrombin acting on 59D8-scuPA-T (FIG. 5). The urokinase activity for both two-chain derivatives reached approximately 100 IU/µg. In the experiment shown in FIG. 5, the molar concentration of thrombin (acting on 59D8-scuPA-T) was three times higher than that of plasmin (acting on 59D8-scuPA). As expected, 59D8-scuPA treated with thrombin and 59D8-scuPA-T treated with plasmin resulted in no urokinase activity.

Activation of Plasminogen

Activation of plasminogen (10–50 µM final concentration) was measured at 37° C. in TNT buffer with 59D8-tcuPA, 59D8-tcuPA-T, or commercially obtained high molecular weight urokinase (Serono; 5 nM final concentration). Generated plasmin at different time intervals (0–5 minutes) was measured using the chromogenic substrate S-2251 (1.0 mM final concentration: Kabi Pharmacia) after 30-fold dilution of the samples.

Activation of plasminogen by 59D8-tcuPA and 59D8-tcuPA-T (the two-chain derivatives of 59D8-scuPA and 59D8-scuPA-T) obeyed Michaelis-Menten kinetics as evidenced by linear double-reciprocal plots of activation rates versus the plasminogen concentration shown in FIG. 6. Although the $k_{cat}$ for both proteins are similar (2.16 sec$^{-1}$ for 59D8-tcuPA and 1.75 sec$^{-1}$ for 59D8-tcuPA-T), the km for 59D8-tcuPA-T (66.3 µM) is approximately three-fold higher than for 59D8-tcuPA (22.5 µM)

In Vitro Clot Lysis Experiments

Human plasma clot lysis assays were performed as described in Runge, supra. Citrated human plasma (pooled from at least 10 healthy donors) was mixed with $^{125}$I-labeled fibrinogen ($2.5 \times 10^6$ cpm/mL: prepared using the lactose peroxidase-glucose oxidase method with Enzymobeads (BioRAD). Each clot was formed using 0.3 mL of the mixture and adding CaCl$_2$ (25 mM final concentration) and human thrombin ($4.5 \times 10^{-3}$ NIHU/mL). For experiments in which the plasminogen activator was added outside the clot, this mixture was pipetted into a 0.2 mL piece of pipet tubing with parafilm on one end, and allowed to clot for at least one hour. The clots were then removed from the pipet pieces to a 4.5-mL polystyrene tube and washed with TNEA buffer (50 mM Tris-HCl, 100 mM NaCl, 1 mM EDTA, 0.01% sodium azide).

Autologous plasma (2 mL) and the plasminogen activator were then added. Heparin (50 U/mL; Elkins-Sinn) was also added in some cases. For experiments in which the plasminogen activator was added to the forming clot, the 0.3 mL mixture was pipetted to the bottom of the polystyrene tube with the plasminogen activator and allowed to clot 10–20 minutes. 2 mL autologous plasma was then added. Both types of clots were rotated at 37° C., and 0.1 mL aliquots were removed at various time points to count the radioactivity on a gamma counter (Packard). High molecular weight scuPA (American Diagnostica) was used as a control in all experiments.

Figure 7A:
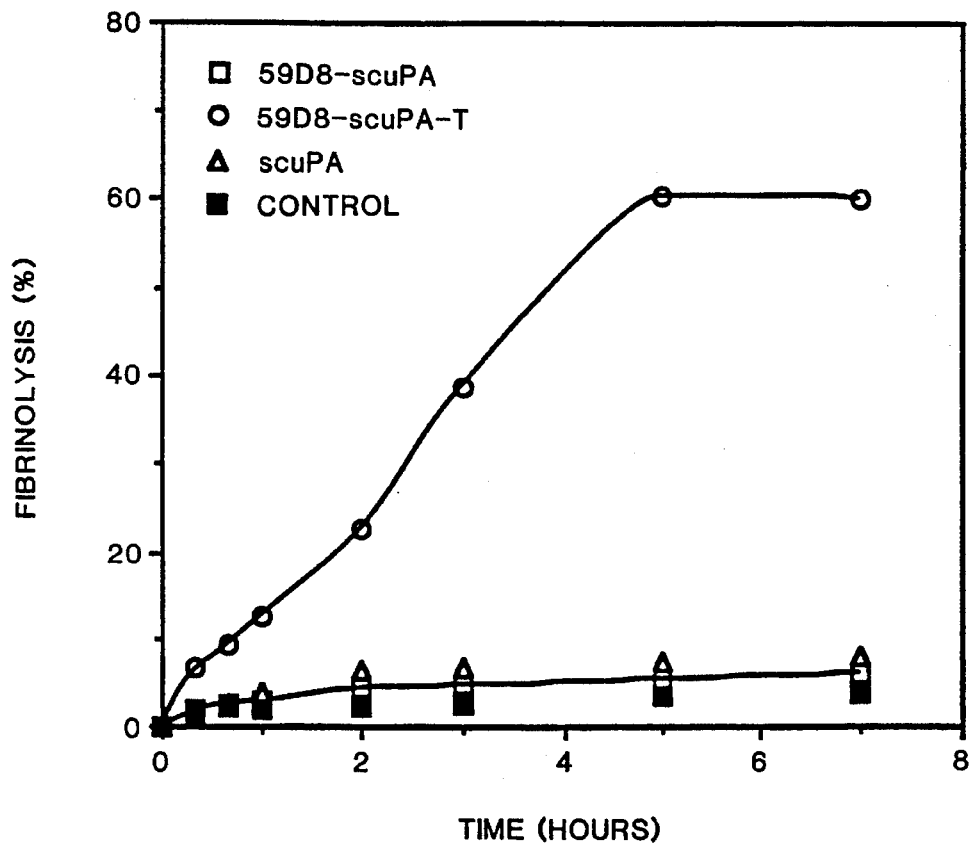
Figure 7B:
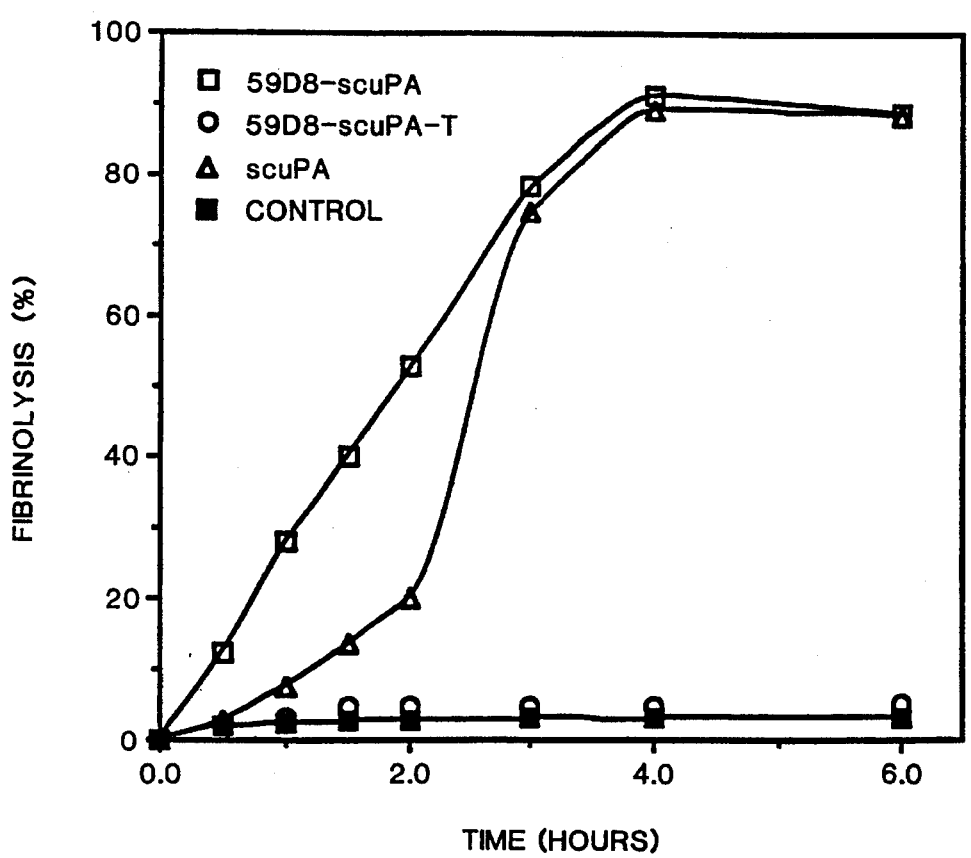

In the experiment shown in FIG. 7A, the plasminogen activator was added to the clot preparation, which was formed using thrombin. 59D8-scuPA-T was able to lyse the clot, indicating that the thrombin cleaved scuPA-T to its active two-chain derivative. When the plasminogen activator was present in the plasma milieu and not in the clot, 59D8-scuPA (and scuPA) was effective at lysing the clot (FIG. 7B). Thrombin inhibitors present in the plasma probably inhibit scuPA-T from being activated and lysing the clot.

Figure 8A:
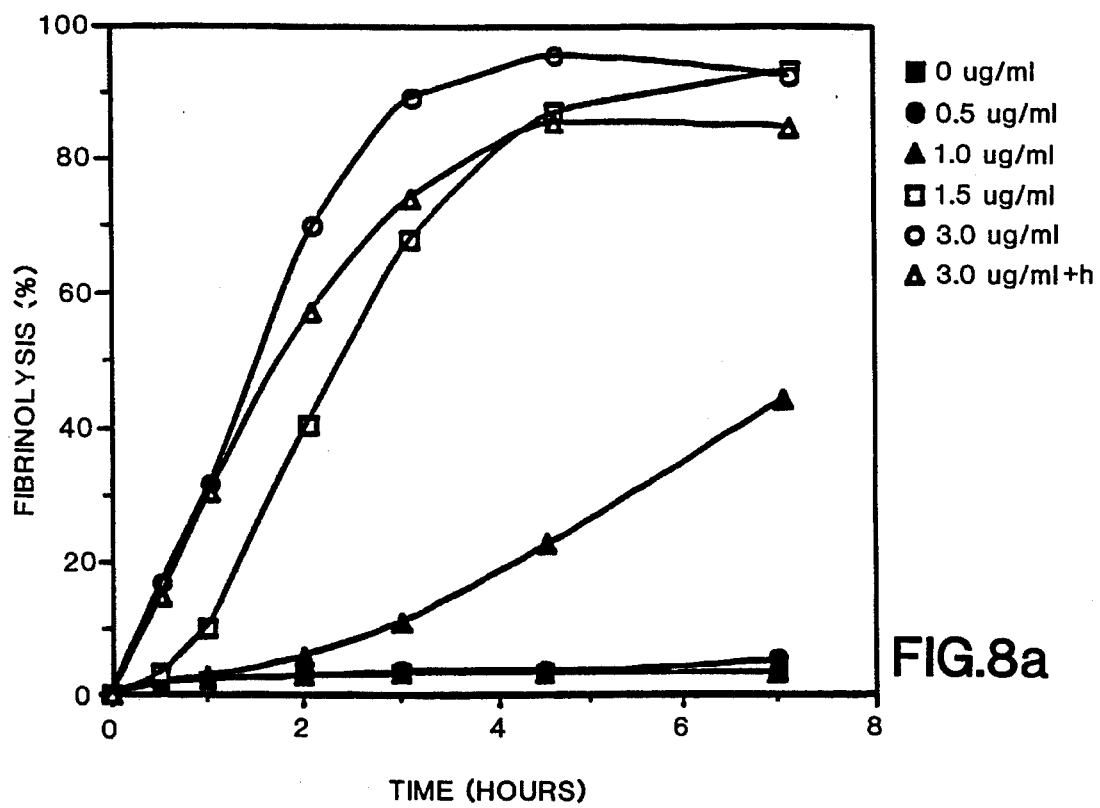
Figure 8B:
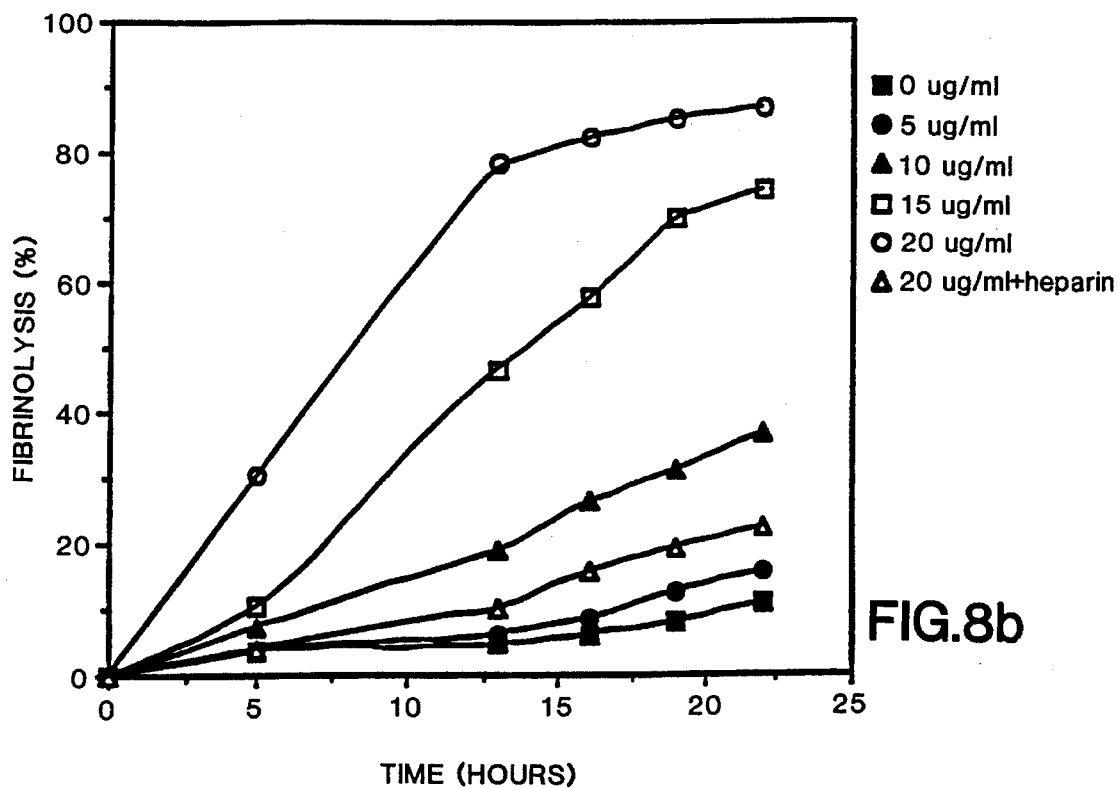

To compare the thrombolytic potency of 59D8-scuPA and 59D8-scuPA-T in the plasma milieu, the concentrations of these proteins were varied in the titration curves shown in FIGS. 8A and B. To reach 30% clot lysis, it took 59D8-scuPA one hour at a concentration of 3 µg/mL, while 59D8-scuPA-T needed five hours at a concentration of 20 µg/mL. Heparin was able to effectively inhibit the activity of 59D8-scuPA-T, but had no effect on 59D8-scuPA.

What is claimed is:

1. A chimeric immunoglobulin molecule comprising
   (a) an antibody variable region having a fibrin-specific antigen binding site and
   (b) a single chain urokinase region having a thrombin activatable site but not a plasmin activatable site.

2. The chimeric immunoglobulin molecule of claim 1 wherein the antibody variable region is from the antibody designated 59D8.

3. A pharmaceutical composition comprising the chimeric immunoglobulin molecule of claim 1 and a pharmaceutically acceptable carrier.

4. A single chain urokinase-type plasminogen activator having a thrombin activatable site but not a plasmin activatable site.

5. The single chain urokinase-type plasminogen activator of claim 4 having a thrombin cleavage site of SEQ. ID. No. 3.

* * * * *